United States Patent [19]
Kalopissis et al.

[11] 3,956,342
[45] May 11, 1976

[54] 4-[4-(2,6-DIAMINOPYRIDYLIMINO)]-2,5-CYCLOHEXADIEN-1-ONE

[75] Inventors: Gregoire Kalopissis, Paris; Andree Bugaut, Boulogne-sur-Seine; Francoise Estradier, Paris, all of France

[73] Assignee: L'Oreal, Paris, France

[22] Filed: May 13, 1974

[21] Appl. No.: 469,497

Related U.S. Application Data

[60] Division of Ser. No. 160,511, July 7, 1971, Pat. No. 3,838,965, which is a continuation-in-part of Ser. No. 97,395, Dec. 11, 1970, abandoned, which is a continuation-in-part of Ser. No. 45,564, June 11, 1970, abandoned.

[30] Foreign Application Priority Data

July 13, 1970 Luxemburg............................ 61316
June 11, 1969 Luxemburg............................ 58848

[52] U.S. Cl............................................. 260/296 R
[51] Int. Cl.²...................................... C07D 213/74
[58] Field of Search ................................ 260/296 R

[56] References Cited
UNITED STATES PATENTS 3,200,040   8/1965   Lange................................. 8/10.2 X

*Primary Examiner*—Henry R. Jiles
*Assistant Examiner*—Bernard Dentz
*Attorney, Agent, or Firm*—Cushman, Darby & Cushman

[57] ABSTRACT

Hair dye and hair setting lotion compositions containing an indoaniline having the formula

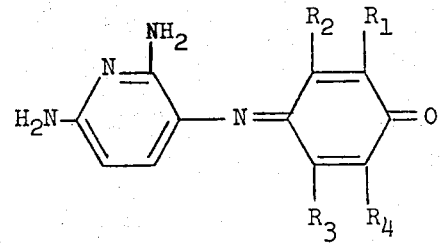

wherein $R_1$, $R_2$, $R_3$ and $R_4$ represents hydrogen, halogen, lower alkyl having 1–4 carbon atoms and lower alkoxy having 1–4 carbon atoms. The indoaniline is prepared by condensing on 2,6-diamino pyridine a corresponding paraminophenol, a salt of the paraminophenol or a corresponding quinonechloroimide.

1 Claim, No Drawings

4-[4-(2,6-DIAMINOPYRIDYLIMINO)]-2,5-CYCLOHEXADIEN-1-ONE

This is a division of application Ser. No. 160,511 filed July 7, 1971, now U.S. Pat. No. 3,838,965 which is a continuation-in-part of our application Ser. No. 97,395, filed Dec. 11, 1970, which in turn is a continuation-in-part of our application Ser. No. 45,564, filed June 11, 1970, which are both now abandoned.

The present invention relates to a new dye composition for keratinous fibers, especially human hair, and, more particularly, to a dye composition containing in solution at least one indoaniline having the formula:

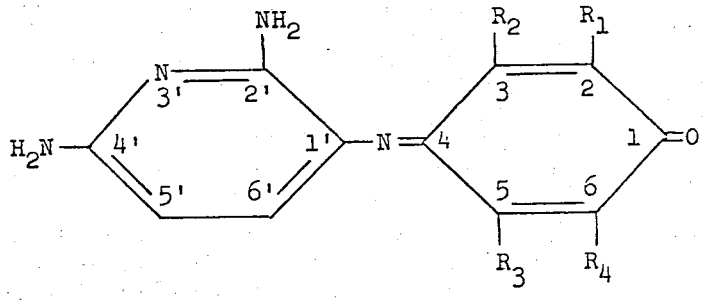

wherein $R_1$, $R_2$, $R_3$ and $R_4$, each independently represent a member selected from the group consisting of hydrogen, halogen, lower alkyl containing 1–4 carbon atoms and lower alkoxy containing from 1 to 4 carbon atoms, it being understood that these compounds can be present in a tautomeric form of that represented by formula I.

The dye compositions of the invention can be aqueous solutions, including aqueous solutions of a lower alkanol. Additionally, the aqueous solutions can include a cosmetic resin, especially when a colored hair setting lotion is contemplated.

The dye composition of the present invention contains from about 0.002–1 percent by weight, preferably between 0.005–0.5 percent by weight of said indoaniline.

The indoaniline as defined above can be used alone, in which case it is possible to obtain on white hair shades rich in glints which range from parme to green, and in particular, very bright blues and silver grays. However, the indoanilines of this invention can also be used in admixture with other capillary dyes such as nitrobenzene, anthraquinone, oxazine and azine dyes. The composition of this invention can also include indophenols, indamines or other indoanilines.

The pH of the dye composition of the present invention can vary within wide limits, and generally the pH will range between 4 and 11, and preferably between 6 and 10.

As stated above, the dye composition of this invention can be in the form of an aqueous solution including an aqueous lower alkanol solution, but it can also contain conventionally employed cosmetic thickeners and thus take the form of creams or gels.

The dye composition of the present invention can additionally include various ingredients that are customarily used in cosmetics, such as wetting agents, dispersants, swelling agents, penetrating agents, emollients or perfumes, and it can also be packaged under pressure in aerosol cans or containers using conventional aerosol propellants such as the chlorofluorohydrocarbons including dichlorodifluoromethane, trichloromonofluoromethane and their mixtures.

The dye composition of the present invention is readily prepared by dissolving in water or in a mixture of water and a lower alkanol such as ethanol and isopropanol, one or more indoanilines as defined above, alone, or in admixture with another dye.

The dyeing of keratinic fibers, particularly human hair, by means of the dye composition of the invention can be effected in the usual way by applying the composition on the fibers that are to be dyed in amounts effective to color the fibers, permitting the composition to remain in contact with the fibers for about 5 to 30 minutes, rinsing the fibers and, if desired, washing the fibers, followed by drying the thus dyed fibers.

When the dye composition of the present invention is to used as a hair setting lotion, the above defined indoaniline is present in amounts generally ranging from about 0.002–0.5 percent by weight of the total composition.

The hair setting lotion also contains a cosmetic film-forming resin in amounts of abouut 1–3 percent by weight of the total composition. Representative cosmetic film-forming resins including polyvinyl pyrrolidone, having a molecular weight ranging from about 10,000 to 700,000, copolymer of crotonic acid and vinyl acetate, copolymer of vinylpyrrolidone and vinyl acetate wherein the ratio of PVP to PVA range between 50–70: 50–30, copolymer of maleic anhydride and butylvinyl ether and the like.

The alcohols suitable for preparation of the hair setting lotions of this invention are lower alkanols, preferably ethanol and isopropanol, which are present in amounts of about 20–70 percent by weight of the total composition. The pH of the hair setting lotion generally ranges between about 5–8.

The hair setting lotions can contain as a coloring agent, only the indoanilines as defined above, if desired, in which case such compositions are termed "shading" compositions which impart to the hair or fibers bright colorings rich in pearly or iridescent glints. However, the hair setting lotion compositions can also contain other direct dyes such as those mentioned above.

These hair setting lotions are utilized in the customary way by applying the same to set wet hair which has been washed and rinsed, followed by rolling up on curlers and drying of the hair.

The indoanilines of this invention can be prepared according to two different processes. One method of producing the indoanilines comprises condensing 2,6-diamino pyridine on a paraaminophenol having the formula:

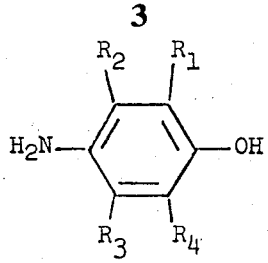

wherein $R_1$, $R_2$, $R_3$ and $R_4$ have the meanings given above, or on a salt of said paraaminophenol. This condensation reaction is effected in an aqueous alkaline medium having a pH ranging from about 9 to 12, in the presence of an oxidizing agent and at a temperature between −5° to 40°C.

The pH of the reaction medium can be adjusted by the incorporation therein of a water soluble alkalinizing agent such as sodium hydroxide, potassium hydroxide and ammonia.

The oxidizing agent used in this condensation reaction can be, for example, hydrogen peroxide, a peroxy salt such as an alkaline persulfate including potassium persulfate and ammonium persulfate, and potassium ferricyanide. The oxidizing agent is generally present in amounts ranging from about 1 to 2 moles per mole of paraaminophenol.

The condensation reaction medium can also include an auxiliary solvent such as a lower alkanol or acetone, in which case the auxiliary solvent can be present in amounts ranging from about 10 to 40 weight percent of the total weight of the solvents.

Representative paraaminophenols that can be used to prepare the indoanilines of the present invention include paraaminophenol, 2-methyl-4-amino phenol, 2,6-dimethyl-4-amino phenol, 3-methyl-4-amino phenol, 3,5-dimethyl-4-amino phenol, 2,3-dimethyl-4-amino phenol, 2-chloro-4-amino phenol and 3-chloro-4-amino phenol.

Representative salts of the paraaminophenol that can be used include the hydrochloride, hydrobromide and sulfate thereof.

The mole ratio of 2,6-diaminopyridine to paraaminophenol can range between about 0.5/1 to 4/1 and is preferably about 1/1.

A second process for producing the indoanilines of the present invention comprises condensing 2,6-diamino pyridine on a quinonechloroimide having the formula:

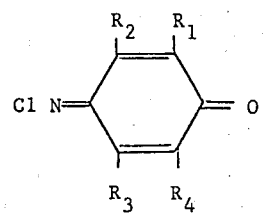

wherein $R_1$, $R_2$, $R_3$ and $R_4$ have the meaning given above. This condensation reaction is effected in an aqueous alkaline medium having a pH ranging from about 8 to 11, and at a temperature between 5°–40°C.

The pH of the reaction medium can be adjusted by the incorporation therein of a water soluble alkalinizing such a sodium hydroxide, potassium hydroxide and ammonia.

The condensation reaction medium can also include an auxiliary solvent such as a lower alkanol or acetone, in which case the auxiliary solvent can be present in amounts ranging from about 20 to 70 weight percent of the total weight of the solvents.

Representative quinonechloroimides that can be used to prepare the indoanilines of the present invention include quinonechloroimide, 2-methyl quinonechloroimide, 3-methyl quinonechloroimide, 2,6-dimethyl quinonechloroimide and 3-chloro quinonechloroimide.

The mole ratio of 2,6-diaminopyridine to quinonechloroimide defined above can range between about 1/1 to 0.5/1 and is preferably 1/1.

The following examples are intended to illustrate the different aspects of the present invention. The temperature indicated in these examples are expressed in degrees Centigrade and, unless otherwise specified, all parts and percentages are by weight.

EXAMPLE 1

N-[(2′,4′-diamino 3′-aza)phenyl] benzoquinone imine is prepared as follows:

Into 250 cc of water to which have been added 100 cc of ammonia at 22°Be, there are dissolved 0.07 mole (7.7 g) of 2,6-diamino pyridine and 0.07 mole (7.6 g) of paraaminophenol. To this solution there is added, little by little, with stirring, 0.07 mole (15.96 g) of ammonium persulfate in solution in 175 cc of water. When the addition is finished, the reaction mixture is left for 15 minutes. The resulting precipitate is filtered, washed with water and dried. 7.6 g of crude aza indoaniline are obtained which, after recrystallization in a dimethylformamide-water mixture, melts at 235°.

| Analysis | Calculated for $C_{11}H_{10}N_4O$ | Found | |
|---|---|---|---|
| C% | 61.68 | 61.23 | 61.15 |
| H% | 4.67 | 4.77 | 4.70 |
| N% | 26.17 | 25.80 | 25.68 |

EXAMPLE 2

Preparation of N-[(2′,4′-diamino-3′-aza) phenyl-] 2-methyl benzoquinone imine.

0.1 mole (12.3 g) of 2-methyl-4-amino phenol is dissolved in 200 cc of 0.5 N soda. To this resulting solution, cooled in ice, there are added, first, 0.1 mole (22.8 g) of ammonium persulfate previously dissolved in 125 cc of water to which is added 50 cc of ammonia at 22°Be then, in a second stage, 0.1 mole (10.9 g) of 2,6-diamino pyridine in solution in 150 cc of water. The resulting precipitate is then filtered, washed with water and dried under a vacuum. 9.14 g of the desired indoaniline, chromatographically pure and which melts at 132° are recovered.

| Molecular mass calculated for $C_{12}H_{12}N_4O$ | | | 228 |
|---|---|---|---|
| Molecular mass found by potentiometric determination in methylisobutylketone by perchloric acid | | | 231 |
| Analysis | Calculated for $C_{12}H_{12}N_4O$ | Found | |
| C% | 63.15 | 62.18 | 62.39 |
| H% | 5.26 | 5.10 | 5.16 |
| N% | 24.56 | 24.16 | 24.39 |

EXAMPLE 3

Preparation of N-[(2',4'-diamino-3'-aza) phenyl-] 2,6-dimethyl benzoquinone imine.

0.1 mole (10.9g) of 2,6-diamino pyridine is dissolved in 125 cc of water, to which are added 100 cc of ammonia at 22°Be. To this resulting solution, cooled in ice, there are added, little by little, with stirring and simultaneously, with the aid of two dropping funnels, on the one hand, 0.025 mole (4.8 g) of monohydrochloride, monohydrate of 2,6-dimethyl-4-amino phenol in solution in 100 cc of water, and on the other hand, 0.025 mole (5.7 g) of ammonium persulate in solution in 20 cc of water. The resulting precipitate obtained is filtered, washed with water and dried. Thus 3 g of crude indoaniline are obtained whose chromatogram reveals the presence of about 10% of a secondary product. When the impure indoaniline is dissolved in a minimum of ethyl alcohol at 25°, cooled to 0° and, little by little, water is added to the alcohol solution, essentially all of the secondary product is precipitated in the form of mordore crystals. This product is chromatographically pure and melts at 170°. Analysis and an RMN [nuclear magnetic resonance] spectrum reveals that it is N-[(3',5'-dimethyl-4'-hydroxy) phenyl] 2,6-dimethyl benzoquinone imine resulting from the oxidation and condensation on it of 2,6-dimethyl-4-amino phenol.

When the crude indoaniline is recrystallized in acetone, the product, which crystallizes by cooling of the acetone solution, is, on the contrary, pure indoaniline (10 g), the secondary product remaining in solution in the mother liquor. The desired indoaniline melts at 210°.

| Analysis | Calculated for $C_{13}H_{14}N_4O$ | Found | |
|---|---|---|---|
| C% | 64.46 | 64.51 | 64.48 |
| H% | 5.78 | 5.85 | 5.75 |
| N% | 23.14 | 23.06 | 23.14 |

EXAMPLE 4

Preparation of N-[(2',4'-diamino-3'-aza) phenyl-] 5-methyl benzoquinone imine.

0.06 mole (6.5 g) of 2,6-diamino pyridine is dissolved in 50 cc of water to which is added 25 cc of ammonia at 22°Be. To this resulting solution, cooled in ice, are added, little by little, with stirring and simultaneously, with two dropping funnels, on the one hand, 0.04 mole (9.12 g) of ammonium persulfate in solution in 50 cc of water, and, on the other hand, 0.04 mole (8.16 g) of 3-methyl-4-amino phenol hydrobromide in solution in 25 cc of water. The resulting precipitate obtained is filtered, washed with water and dried. Thus 4.2 g of the desired indoaniline are obtained which, after recrystallization in a dimethylformamide-water mixture, melts with decomposition at 142°.

| | | | |
|---|---|---|---|
| Molecular mass calculated for $C_{12}H_{12}N_4O$ | | | 228 |
| Molecular mass found by potentiometric determination in acetic acid by perchloric acid | | | 232 |
| Analysis | Calculated for $C_{12}H_{12}N_4O$ | Found | |
| C% | 63.15 | 62.84 | 62.80 |
| H% | 5.26 | 5.33 | 5.24 |
| N% | 24.56 | 24.22 | 24.29 |

EXAMPLE 5

Preparation of N-[(2',4'-diamino-3'-aza) phenyl-] 5-chloro benzoquinone imine.

0.036 mole (3.9 g) of 2,6-diamino pyridine is dissolved in 30 cc of water to which are added 20 cc of ammonia at 22°Be. To this resulting solution, cooled in ice, there are added, little by little, with stirring and simultaneously, with the aid of two dropping funnels, on the one hand, 0.03 mole (6.84 g) of ammonium persulfate in solution in 25 cc of water, and, on the other hand, 0.03 mole (5.4 g) of 3-chloro-4-amino phenol hydrochloride in solution in 50 cc of water. The resulting precipitate obtained is filtered, washed with water and dried. Thus, 3.6 g of the desired indoaniline are obtained in the form of mordore green crystals. After recrystallization in a dimethylformamide-water mixture, the product melts with decomposition at 248°.

| | | | |
|---|---|---|---|
| Molecular mass calculated for $C_{11}H_9ClN_4O$ | | | 248.5 |
| Molecular mass found by potentiometric determination in acetic acid by perchloric acid | | | 249 |
| Analysis | Calculated for $C_{11}H_9ClN_4O$ | Found | |
| C% | 53.11 | 53.32 | 53.38 |
| H% | 3.62 | 3.72 | 3.69 |
| N% | 22.53 | 22.27 | 22.25 |

EXAMPLE 6

Preparation of N-[(2',4' diamino-3'-aza) phenyl-] 2,5-dimethyl benzoquinone imine having the formula:

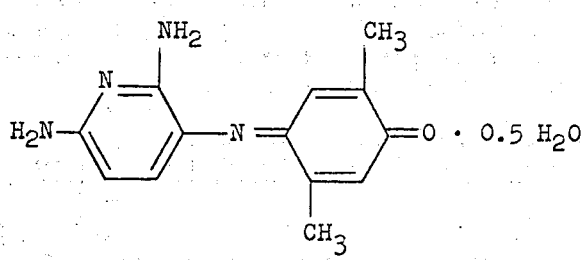

Initially, 0.02 mole (2.74 g) of 2,5-dimethyl-4-amino phenol is dissolved in 50 cc of 4 N soda solution. Then, 0.02 mole (2.18 g) of 2,6-diamino pyridine is dissolved in 50 cc of water. The two solutions thus prepared are mixed. The mixture is cooled to 0°C and 0.02 mole (4.56 g) of ammonium persulfate in solution in 50 cc of water is added. The reaction mixture is left for an hour at 0°. The desired azaindoaniline precipitates and the resulting precipitate is filtered. After washing the precipitate with water and drying the same under a vacuum, it is chromatographically pure and melts at 238°.

| Molecular mass calculated for $C_{13}H_{14}N_4O$, 0.5 $H_2O$ | | 251 | |
|---|---|---|---|
| Molecular mass found by potentiometric determination in acetic acid by perchloric acid | | 246 | |
| Analysis | Calculated for $C_{13}H_{14}N_4O$ 0.5 $H_2O$ | Found | |
| C% | 62.15 | 62.22 | 62.65 |
| H% | 5.97 | 5.74 | 5.85 |
| N% | 22.31 | 22.42 | 22.19 |

EXAMPLE 7

Preparation of N-[(2′,4′-diamino-3′-aza) phenyl-] 2-chloro benzoquinone imine.

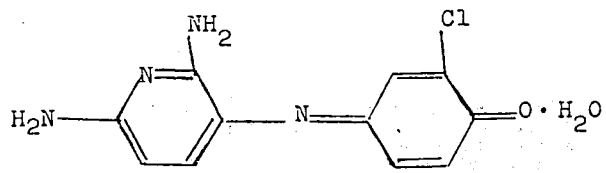

0.02 mole (3.6 g) of 2-chloro-4-amino phenol hydrochloride is dissolved in 80 cc of water. Then, 0.02 mole (2.18 g) of 2,6-diamino pyridine is dissolved in 100 cc of water. The two solutions thus prepared are mixed. To this mixture, previously cooled to 0°, there is added 0.02 mole (4.56 g) of ammonium persulfate in solution in 50 cc of water to which are added 25 cc of ammonia at 22°Be. The desired azaindoaniline rapidly precipitates in the form of green crystals with golden glints. The supernatant liquid is centrifuged, decanted and the precipitate is washed three times in ice water by successive centrifugings and decantings. After drying under vacuum, the product obtained (2.7 g) is chromatographically pure and melts at 250°.

| Analysis | Calculated for $C_{11}H_9N_4O$ Cl. $H_2O$ | Found | |
|---|---|---|---|
| C% | 49.53 | 49.37 | 49.72 |
| H% | 4.12 | 4.17 | 4.18 |
| N% | 21.01 | 20.90 | 20.84 |

EXAMPLE 8

Preparation of N-[(2′,4′-diamino-3′-aza) phenyl-] 2,3-dimethyl benzoquinone imine having the formula:

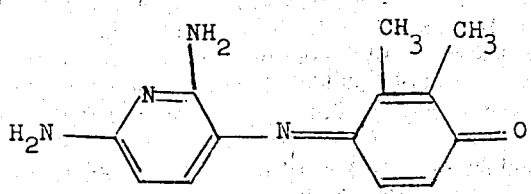

0.02 mole (2.74 g) of 2,3-dimethyl-4-amino phenol is dissolved in 30 cc of a normal soda solution. Then 0.02 mole (2.18 g) of 2,6-diamino pyridine is dissolved in 100 cc of water. The two solutions thus prepared are mixed. After the mixture is cooled to 0°C there is then added 0.02 mole (4.56 g) of ammonium persulfate in solution in 50 cc of water to which are added 20 cc of ammonia at 22°Be. The reaction mixture is left for 20 minutes at 0°. The desired azaindoaniline, crystallized in the form of green crystals with golden glints (2.3 g), is filtered. After recrystallization in a dimethylformamide-water mixture, the product is chromatographyically suitable and metls at 242°.

| Analysis | Calculated for $C_{13}H_{14}N_4O$ | Found | |
|---|---|---|---|
| C% | 64.46 | 64.76 | 64.21 |
| H% | 5.78 | 5.88 | 5.82 |
| N% | 23.14 | 23.22 | 23.11 |

EXAMPLE 9

Preparation of N-[(2′,4′-diamino-3′-aza) phenyl-] 3,5-dimethyl benzoquinone imine.

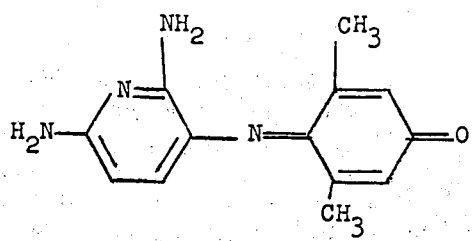

0.02 mole (2.74 g) of 3,5-dimethyl-4-amino phenol is dissolved in 50 cc of a normal soda solution. Then 0.02 mole (2.18 g) of 2,6-diamino pyridine is dissolved in 60 cc of water. The two solutions thus prepared are mixed. To the resulting mixture, cooled to 0°, there is added 0.02 mole (4.56 g) of ammonium persulfate in solution in 50 cc of water. The reaction mixture is left for 20 minutes at 0°C. The desired azaindoaniline precipitates and is filtered, washed with water and dried under a vacuum. The product is chromatographically pure and melts at 211°.

Molecular mass calculated for $C_{13}H_{14}N_4O$.     242

Molecular mass found by potentiometric determination in methylisobutylketone by perchloric acid.     245

EXAMPLE 10

Preparation of N-[(2',4'-diamino-3'-aza) phenyl-] 5-methyl benzoquinone imine having the formula:

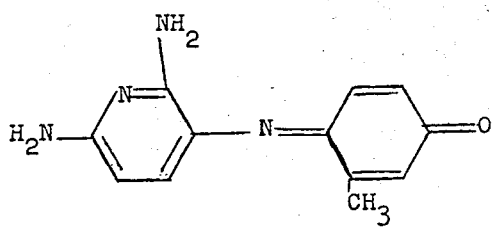

0.01 mole (1.55 g) of 3-methyl quinonechloroimide is dissolved in 30 cc of ethyl alcohol. Then 0.01 mole (1.09 g) of 2,6-diamine pyridine is dissolved in 10 cc of water to which have been added 10 cc of ammonia at 20°Be and 1 cc of normal soda solution. The two solutions, previously cooled, are mixed and the mixture is left for an hour at ambient temperature. 50 cc of ice water are added and 0.85 g of the desired indoaniline precipitate and are filtered which after washing with water and ethyl alcohol and drying under a vacuum, melt at 114° (no lowering of the melting point used in mixture with the product of example 4).

Molecular mass calculated for $C_{12}H_{12}N_4O$.     228

Molecular mass found by potentiometric determination in acetic acid by perchloric acid.     234

EXAMPLE 11

Preparation of N-[(2',4' diamino-3'-aza) phenyl-] 5-chlorobenzoquinone imine having the formula:

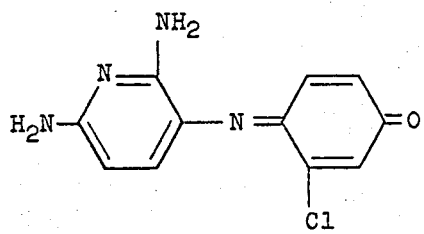

0.01 mole (1.76 g) of 3-chloro quinonechloroimide is dissolved in 30 cc of ethyl alcohol. Then 0.01 mole (1.09 g) of 2,6-diamino pyridine is dissolved in 10 cc of water to which are added 10 cc of ammonia at 22°Be and 1 cc of normal soda solution. The resulting two previously cooled solutions are mixed and this reaction mixture is left for 20 minutes at ambient temperature. The desired indoaniline (1.5 g) precipitates and is filtered, washed with water then with acetone and, after drying under a vacuum, it melts at 246° (no lowering of the melting point used in mixture with the product of example 5).

Molecular mass calculated for $C_{11}H_9Cl\ N_4O$.     248.5

Molecular mass found by potentiometric determination in acetic by perchloric acid.     252

EXAMPLE 12

The following hair dye composition is prepared:

| | |
|---|---|
| The indoaniline of Example 2 | 0.1 g |
| 96° ethyl alcohol | 20 g |
| Ammonia at 22°Be sufficient for pH 10 | |
| Water, sufficient for | 100 g |

This hair dye composition, when applied to 95% naturally white hair for 20 minutes, imparts thereto, after rinsing and shampooing, a blue green coloring.

EXAMPLE 13

The following hair dye composition is prepared:

| | |
|---|---|
| The indoaniline of Example 2 | 0.1 g |
| 96° ethyl alcohol | 20 g |
| 1% lactic acid solution sufficient for pH 5 | |
| Water sufficient for | 100 g |

This hair dye composition, when applied to 95% naturally white hair for 20 minutes, imparts thereto, after rinsing and shampooing, a clear silvery turquoise coloring.

EXAMPLE 14

The following hair dye composition is prepared:

| | |
|---|---|
| The indoaniline of Example 2 | 0.05 g |
| Butylglycol | 5 g |
| Lauryl alcohol oxyethylenated with 10.5 moles of ethylene oxide | 5 g |
| Water, sufficient for | 100 g |

This hair dye composition, which has a pH of 7, is applied to 95% naturally white hair for 20 minutes. After rinsing and shampooing, a pearly bluish clear green coloring is obtained.

EXAMPLE 15

The following hair setting lotion is prepared:

| | |
|---|---|
| The indoaniline of Example 2 | 0.2 g |
| Crotonic acid-vinyl acetate copolymer (10%/90% - molecular weight 45,000) | 2 g |
| 96° ethyl alcohol | 50 g |
| Triethanolamine, sufficient for pH 7 | |
| Water, sufficient for | 100 g |

This hair setting lotion, applied to 100% white bleached hair, imparts thereto an intense ultramarine coloring. When applied to 95% naturally white hair, it imparts thereto an ultramarine coloring with silvery glints.

EXAMPLE 16

The following hair setting lotion is prepared:

| | |
|---|---|
| The indoaniline of Example 2 | 0.4 g |
| Crotonic acid-vinyl acetate copolymer (10%/90% - molecular weight 45,000) | 2 g |
| 96° ethyl alcohol | 50 g |
| Triethanolamine, sufficient for pH 7 | |
| Water, sufficient for | 100 g |

This hair setting lotion is applied to brown hair and imparts thereto a brownish black coloring with irridescent glints.

EXAMPLE 17

The following hair setting lotion is prepared:

| | |
|---|---|
| The indoaniline of Example 2 | 0.015 g |
| N-[(4'-hydroxy)phenyl-] 3-amino-6-methyl benzoquinone imine | 0.1 g |
| Crotonic acid-vinyl acetate copolymer (10%/90% - molecular weight 48,000) | |
| 96° ethyl alcohol | 50 g |
| Triethanolamine, sufficient for pH 7 | |
| Water, sufficient for | 100 g |

This hair setting lotion is applied to 100% white bleached hair and imparts thereto a dark golden blond coloring.

EXAMPLE 18

The following hair dye composition is prepared:

| | |
|---|---|
| The indoaniline of Example 2 | 0.05 g |
| Nitroparaphenylenediamine | 0.2 g |
| 96° ethyl alcohol | 50 g |
| Ammonia at 22°Be, sufficient for pH 8 | |
| Water, sufficient for | 100 g |

The hair dye composition is applied to 60% naturally white hair and imparts thereto a dark brown coloring with copper glints.

EXAMPLE 19

The following hair setting lotion is prepared:

| | |
|---|---|
| The indoaniline of Example 2 | 0.04 g |
| N-[(2',4'-diamino-5'-methoxy)phenyl] benzoquinone imine trihydrate | 0.1 g |
| Crotonic acid-vinyl acetate copolymer (10%/90% - molecular weight 50,000) | 2 g |
| 96° ethyl alcohol | 50 g |
| Triethanolamine, sufficient for pH 7 | |
| Water, sufficient for | 100 g |

This hair setting lotion is applied to 100% white bleached hair and imparts thereto a clear brown-purple shade with pearly glints.

EXAMPLE 20

The following hair setting lotion is prepared:

| | |
|---|---|
| The indoaniline of Example 3 | 0.1 g |
| Crotonic acid-vinyl acetate copolymer (10%/90% - molecular weight 50,000) | 2 g |
| 96° ethyl alcohol | 50 g |
| Triethanolamine, sufficient for pH 7 | |
| Water, sufficient for | 100 g |

This hair setting lotion is applied to 100% white bleached hair and imparts thereto a very brilliant intense pure blue shade. This same solution is then applied to 95% naturally white hair and imparts thereto a pure blue shade with silvery glints.

EXAMPLE 21

The following hair setting lotion is prepared:

| | |
|---|---|
| The indoaniline of Example 3 | 0.03 g |
| N-[(3',5'-dimethyl-4'hydroxy) phenyl] 2,6-dimethyl benzoquinone imine | 0.1 g |
| Crotonic acid-vinyl acetate copolymer (10%/90% - molecular weight 48,000) | 2 g |
| 96° ethyl alcohol | 50 g |
| Triethanolamine, sufficient for pH 7 | |
| Water, sufficient for | 100 g |

This hair setting lotion is applied to 100% white bleached hair and imparts thereto a mauve coloring.

EXAMPLE 22

The following hair dye composition is prepared:

| | |
|---|---|
| The indoaniline of Example 3 | 0.1 g |
| 96° ethyl alcohol | 20 g |
| Ammonia at 22°Be, sufficient for pH 10 | |
| Water, sufficient for | 100 g |

This hair dye composition is applied to 95% naturally white hair for 10 minutes and imparts thereto, after rinsing and shampooing, a Cyprian green coloration.

EXAMPLE 23

The following hair dye composition is prepared:

| | |
|---|---|
| The indoaniline of Example 3 | 0.1 g |
| 96° ethyl alcohol | 20 g |
| 1% lactic acid solution in water, sufficient for pH 5 | |
| Water, sufficient for | 100 g |

This hair dye composition is applied to 95% naturally white hair for 15 minutes and imparts thereto, after rinsing and shampooing, a clear Cyprian green coloring.

EXAMPLE 24

The following hair dye composition is prepared:

| | |
|---|---|
| The indoaniline of Example 1 | 0.25 g |
| 96° isopropyl alcohol | 20 g |
| Ammonia at 22°Be, sufficient for pH 10.5 | |
| Water, sufficient for | 100 g |

This hair dye composition is applied to 95% naturally white hair for 25 minutes and imparts thereto a clear green bluish coloring.

EXAMPLE 25

The following hair dye composition is prepared:

| | |
|---|---|
| The indoaniline of Example 1 | 0.1 g |
| 96° ethyl alcohol | 20 g |
| 1% lactic acid solution in water sufficient for pH 5 | |
| Water, sufficient for | 100 g |

This hair dye composition is applied to 95% naturally white hair for 25 minutes and imparts thereto a silvery gray coloring with slight mauve glints.

EXAMPLE 26

The following hair setting lotion is prepared:

| | |
|---|---|
| The indoaniline of Example 1 | 0.1 g |
| Crotonic acid-vinyl acetate copolymer (10%/90% - molecular weight 45,000) | 2 g |
| 96° ethyl alcohol | 50 g |
| Triethanolamine, sufficient for pH 7 | |
| Water, sufficient for | 100 g |

This hair setting lotion is applied to 100% white bleached hair and imparts thereto an iridescent parme coloring. This same hair lotion is also applied to 95% naturally white hair and imparts thereto a slate blue coloring.

EXAMPLE 27

The following hair setting lotion is prepared:

| | |
|---|---|
| The indoaniline of Exaple 4 | 0.1 g |
| Crotonic acid-vinyl acetate copolymer (10%/90% - molecular weight 45,000) | 2 g |
| 96° ethyl alcohol | 50 g |
| Triethanolamine, sufficient for pH 7 | |
| Water, sufficient for | 100 g |

This hair setting lotion is applied to 100% white bleached hair and imparts thereto a bright blue shade with parme glints. This same hair setting lotion is also applied to 95% naturally white hair and imparts thereto a myosotis blue shade with silvery glints.

EXAMPLE 28

The following hair dye composition is prepared:

| | |
|---|---|
| The indoaniline of Example 4 | 0.1 g |
| 96° Ethyl alcohol | 30 g |
| Ammonia, at 22°Be sufficient for pH 10 | |
| Water, sufficient for | 100 cc |

This hair dye composition is applied to 95% naturally white hair for 20 minutes, and imparts thereto, after rinsing and shampooing, a strongly silvered clear blue coloring.

EXAMPLE 29

The following hair setting lotion is prepared:

| | |
|---|---|
| The indoaniline of Example 5 | 0.1 g |
| Crotonic acid-vinyl acetate copolymer (10%/90% - molecular weight 50,000) | 2 g |
| 96° ethyl alcohol | 50 g |
| Triethanolamine, sufficient for pH 7 | |
| Water, sufficient for | 100 g |

This hair setting lotion is applied to 100% white bleached hair and imparts thereto a clear parme shade. This same hair setting lotion is also applied to 95% naturally white hair and imparts thereto a silvery blue gray shade.

EXAMPLE 30

The following hair dye composition is prepared:

| | |
|---|---|
| The indoaniline of Example 6 | 0.25 g |
| 96° ethyl alcohol | 25 g |
| Water, sufficient for | 100 g |
| Ammonia, at 22°Be sufficient for pH 10 | |

The hair dye composition is applied to 95% naturally white hair for 20 minutes at ambient temperature and imparts thereto, after rinsing and shampooing, a strongly pearly clear turquoise blue coloring.

EXAMPLE 31

The following hair setting lotion is prepared:

| | |
|---|---|
| Dye of Example 6 | 0.10 g |
| Copolymer of 10% crotonic acid - 90% vinyl acetate (molecular weight 45,000 – 50,000) | 2 g |
| 96° ethyl alcohol | 50 g |
| Water, sufficient for | 100 g |
| Triethanolamine, sufficient for pH 7 | |

This hair setting lotion is applied to 100% white bleached hair and imparts thereto a strongly silvered myosotis blue shade.

EXAMPLE 32

The following hair dye composition is prepared:

| | |
|---|---|
| The indoaniline of Example 6 | 0.2 g |
| 96° ethyl alcohol | 20 g |
| Water, sufficient for | 100 g |
| 10% lactic acid in water, sufficient for pH 4.2 | |

This hair dye composition is applied to 95% naturally white hair for 20 minutes at ambient temperature and imparts thereto, after rinsing and shampooing, a silvery blue gray coloration.

EXAMPLE 33

The following hair setting lotion is prepared:

| | |
|---|---|
| The indoaniline of Example 7 | 0.05 g |
| Vinyl acetate-crotonic acid copolymer (as in Example 31) | 2 g |
| 96° ethyl alcohol | 50 g |
| Water, sufficient for | 100 g |
| Triethanolamine, sufficient for pH 7 | |

This hair setting lotion is applied to 100% white bleached hair and imparts thereto a very bright emerald green shade.

EXAMPLE 34

The following hair setting lotion is prepared:

| | |
|---|---|
| The indoaniline of Example 7 | 0.025 g |
| N-[(3',5'-dimethyl-4'-hydroxy)phenyl-] 2,6-dimethyl benzoquinone imine | 0.05 g |
| Vinyl acetate-crotonic acid copolymer (of Example 31) | 2 g |
| 96° ethyl alcohol | 50 g |
| Water, sufficient for | 100 g |
| Triethanolamine, sufficient for pH 7 | |

This hair setting lotion is applied to 100% white bleached hair and imparts thereto an ash gray shade with slight mauve glints.

EXAMPLE 35

The following hair setting lotion is prepared:

| | |
|---|---|
| The indoaniline of Example 8 | 0.005 g |
| Vinyl acetate-crotonic acid copolymer (as in Example 31) | 2 g |
| 96° ethyl alcohol, sufficient for | 50 g |
| Water, sufficient for | 100 g |
| Triethanolamine, sufficient for pH 7 | |

This hair setting lotion is applied to 100% white bleached hair and imparts thereto a pearly appearance with slight green glints.

EXAMPLE 36

The following hair dye composition is prepared:

| | |
|---|---|
| The indoaniline of Example 8 | 0.1 g |
| 96° ethyl alcohol | 30 g |
| Water, sufficient for | 100 g |

-continued

The pH of the solution is equal to 7.

This hair dye composition is applied to 95% naturally white hair for 20 minutes at ambient temperature and imparts thereto, after rinsing and shampooing, a silvery blue gray coloring.

EXAMPLE 37

The following hair setting lotion is prepared:

| | |
|---|---|
| The indoaniline of Example 9 | 0.05 g |
| Vinyl acetate-crotonic acid copolymer (as in Example 31) | 2 g |
| 96° ethyl alcohol | 50 g |
| Water, sufficient for | 100 g |
| Triethanolamine, sufficient for pH 7 | |

This hair setting lotion is applied to 100% white bleached hair and imparts thereto a silver gray shade with slight blue glints.

EXAMPLE 38

The following hair dye composition is prepared:

| | |
|---|---|
| The indoaniline of Example 9 | 0.05 g |
| 96° ethyl alcohol | 30 g |
| Water, sufficient for | 100 g |

-continued

Ammonia, at 22°Be sufficient for pH 10

This hair dye composition is applied to 95% naturally white hair for 10 minutes at ambient temperature and imparts thereto, after rinsing and shampooing, a silver gray shade with green glints.

What is claimed is:

1. An indoaniline having the formula

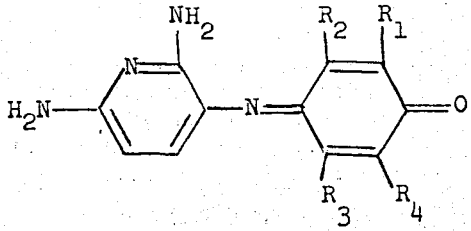

wherein $R_1$, $R_2$, $R_3$ and $R_4$, each independently represent a member selected from the group consisting of hydrogen, halogen, lower alkyl having 1–4 carbon atoms and lower alkoxy having 1 to 4 carbon atoms, and the tautomeric forms thereof.

* * * * *